(12) United States Patent
Rondeau et al.

(10) Patent No.: US 6,190,421 B1
(45) Date of Patent: *Feb. 20, 2001

(54) METHOD FOR DYEING KERATIN FIBRES WITH OXIDATION DYE PRECURSORS AND DIRECT POWDER DYES

(75) Inventors: Christine Rondeau, Sartrouville; Nicole Zemori, Les Lilas, both of (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/171,713
(22) PCT Filed: Apr. 11, 1997
(86) PCT No.: PCT/FR97/00650
§ 371 Date: Dec. 15, 1998
§ 102(e) Date: Dec. 15, 1998
(87) PCT Pub. No.: WO97/39727
PCT Pub. Date: Oct. 30, 1997

(30) Foreign Application Priority Data

Apr. 25, 1996 (FR) .................................. 96 05252

(51) Int. Cl.⁷ .................................................. A61K 7/13
(52) U.S. Cl. .......................... 8/407; 8/408; 8/426; 8/524
(58) Field of Search ................................ 8/407, 408, 414, 8/415, 426, 524, 527

(56) References Cited

U.S. PATENT DOCUMENTS

| | | | |
|---|---|---|---|
| 3,578,387 | * | 5/1971 | Zviak et al. ............................ 8/431 |
| 4,025,301 | * | 5/1977 | Lang ....................................... 8/405 |
| 4,931,066 | * | 6/1990 | Grollier et al. ......................... 8/410 |
| 4,961,925 | * | 10/1990 | Tsujino et al. .......................... 8/406 |
| 5,053,051 | * | 10/1991 | Tennigkeit et al. ..................... 8/406 |
| 5,261,926 | * | 11/1993 | Lang et al. .............................. 8/406 |
| 5,275,626 | * | 1/1994 | Grollier .................................. 8/406 |
| 5,279,616 | * | 1/1994 | Lang et al. .............................. 8/406 |
| 5,374,288 | * | 12/1994 | Prota et al. ............................. 8/406 |
| 5,435,810 | * | 7/1995 | Prota et al. ............................. 8/406 |
| 5,441,542 | * | 8/1995 | Prota et al. ............................. 8/406 |
| 5,849,041 | * | 12/1998 | Kunz et al. ............................. 8/408 |

FOREIGN PATENT DOCUMENTS

| | | |
|---|---|---|
| 2 359 399 | 6/1975 | (DE) . |
| 3 814 685 | 9/1988 | (DE) . |
| 3 843 892 | 6/1990 | (DE) . |
| 4 133 957 | 4/1993 | (DE) . |
| 1 026 978 | 4/1966 | (GB) . |
| 1 153 196 | 5/1969 | (GB) . |
| 2 093 867 | 9/1982 | (GB) . |
| 2 093 868 | 9/1982 | (GB) . |
| 2 192 645 | 1/1988 | (GB) . |
| 63-169571 | 7/1988 | (JP) . |
| 3-33495 | 2/1991 | (JP) . |
| WO 94/08969 | 4/1994 | (WO) . |
| WO 94/08970 | 4/1994 | (WO) . |
| WO 95/01772 | 1/1995 | (WO) . |
| WO 95/15144 | 6/1995 | (WO) . |

OTHER PUBLICATIONS

English Language Derwent Abstract of DE 3 259 399, Jun. 1975.
English Language Derwent Abstract of DE 3 814 685, Sep. 1988.
English Language Derwent Abstract of DE 3 843 892, Jun. 1990.
English Language Derwent Abstract of DE 4 133 957, Apr. 1993.
English Language Derwent Abstract of JP 63–169571, Jan. 1990.

* cited by examiner

Primary Examiner—Caroline D. Liott
(74) Attorney, Agent, or Firm—Finnegan Henderson Farabow Garrett & Dunner, L.L.P.

(57) ABSTRACT

A method for dyeing keratin fibers, particularly human keratin fibers, and more particularly hair. When the method is used, an extemporaneous mixture is applied on the fibers of a composition (A) containing one or more oxidation dye precursors and optionally one or more couplers, of a composition (B), in powder form, containing one or more direct dyes, preferably cationic, optionally dispersed in an organic pulverulent excipient and/or a mineral pulverulent excipient, and a composition (C) containing one or more oxidizing agents. The invention also features a ready-to-use composition of three components (A), (B), and (C) stored separately and mixed at the time of use to be applied on keratin fibers.

40 Claims, No Drawings

METHOD FOR DYEING KERATIN FIBRES WITH OXIDATION DYE PRECURSORS AND DIRECT POWDER DYES

The invention relates to a process for dyeing keratin fibres, in particular human keratin fibres and especially the hair, characterized in that an extemporaneous mixture is applied to the keratin fibres at the time of use, this mixture comprising: a composition (A) containing at least one oxidation dye precursor and optionally at least one coupler, a powdered composition (B) containing at least one direct dye, and a composition (C) containing at least one oxidizing agent.

The use of oxidation dye precursors is widespread in the field of hair dyeing. This class of dyes comprises compounds that are initially colourless or only faintly coloured, commonly referred to as "oxidation bases", which develop their dyeing power on the hair in the presence of oxidizing agents, leading to the formation of coloured compounds. The formation of these coloured compounds results either from an oxidative condensation of the oxidation bases with themselves, or from an oxidative condensation of the oxidation bases with coloration modifiers, commonly referred to as "couplers", which are generally present in the dye compositions used in oxidation dyeing.

The variety of molecules used, which consist, on the one hand, of the oxidation bases, and, on the other hand, of the couplers, produces a very wide range of colours.

In order further to vary the shades obtained and to give them glints, it is also well known to use, in combination with oxidation dye precursors and couplers, direct dyes, i.e. coloured substances which provide a coloration in the absence of oxidizing agent.

However, the conventional use, i.e. in the same dye composition, of oxidation dye precursors and direct dyes, such as, in particular, most nitrobenzenes, is limited by the fact that these direct dyes are particularly reactive towards the reducing agents which generally need to be added to compositions containing oxidation dye precursors in order to prevent premature oxidation of the said precursors before the moment chosen for the development of the coloration on the hair, for example during storage.

This reactivity towards the reducing agents is reflected by a gradual loss or a change in the dyeing power of the direct dyes during storage of the dye compositions before they are used.

In addition, the conventional use of direct dyes is limited in terms of concentration in the composition for reasons of solubility of the said dyes in the dye support. The result of this is that the dyeing power of the compositions obtained is often limited.

To overcome these drawbacks, the Applicant has conducted considerable research in this matter, and has now discovered, surprisingly, that it is possible to use direct dyes at higher concentrations than those in the prior art, and to obtain strong dyes, which also show good resistance towards atmospheric agents such as light and bad weather, and towards perspiration and the various treatments to which the hair may be subjected (washing, permanent-waving), using, at the time of use, an extemporaneous mixture of three separately prepackaged components (A), (B) and (C), in which (A) contains the oxidation dye precursor and optionally the coupler, (B) contains the direct dye, in powder form or dispersed in an organic excipient and/or an inorganic pulverulent excipient in powder form, and (C) contains the oxidizing agent.

This invention also allows better conservation of the dyeing power of the compositions.

This discovery forms the basis of the present invention.

The subject of the present invention is thus a process for dyeing keratin fibres, in particular human keratin fibres and especially the hair, characterized in that an extemporaneous mixture is applied to the keratin fibres at the time of use, this mixture comprising three compositions (A), (B) and (C) below:

a composition (A) containing at least one oxidation dye precursor and optionally at least one coupler, in a medium which is suitable for dyeing, a composition (B) in powder form, containing at least one direct dye, optionally dispersed in an organic pulverulent excipient and/or an inorganic pulverulent excipient, and a composition (C) containing at least one oxidizing agent in a medium which is suitable for dyeing.

The subject of the invention is also a ready-to-use composition containing three components (A), (B) and (C) which are stored separately and mixed at the time of use, for application to keratin fibres.

Another subject of the invention relates to multicompartment devices or "kits" for dyeing keratin fibres, characterized in that they contain at least three compartments, one of which contains a composition (A) containing at least one oxidation dye precursor and optionally at least one coupler, in a medium which is suitable for dyeing, a second contains a composition (B), in powder form, containing at least one direct dye, in powder form or dispersed in an organic pulverulent excipient and/or an inorganic pulverulent excipient, and a third contains a composition (C) containing at least one oxidizing agent in a medium which is suitable for dyeing.

However, other characteristics, aspects, objects and advantages of the invention will become even more apparent on reading the description and the examples which follow.

The oxidation dye precursors which can be used in the dyeing process according to the invention are those used conventionally in oxidation dye compositions, i.e. ortho- or para-phenylenediamines, bis(phenyl)alkylenediamines, ortho- or para-aminophenols, or heterocyclic bases, as well as the addition salts of these compounds with an acid.

Among the para-phenylenediamines which can be used as oxidation bases in the dyeing process according to the invention, mention may be made in particular of the compounds corresponding to formula (I) below, and the addition salts thereof with an acid:

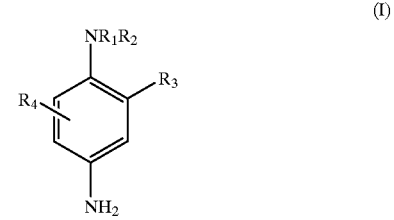

(I)

in which: $R_1$, represents a hydrogen atom or a $C_1$–$C_4$ alkyl, $C_1$–$C_4$ monohydroxyalkyl, $C_2$–$C_4$ polyhydroxyalkyl or $(C_1$–$C_4)$alkoxy$(C_1$–$C_4)$alkyl radical, $R_2$ represents a hydrogen atom or a $C_1$–$C_4$ alkyl, $C_1$–$C_4$ monohydroxyalkyl or $C_2$–$C_4$ polyhydroxyalkyl radical, $R_3$ represents a hydrogen atom, a halogen atom such as a chlorine atom, or a $C_1$–$C_4$ alkyl, sulpho, carboxyl, $C_1$–$C_4$ monohydroxyalkyl or $C_1$–$C_4$ hydroxyalkoxy radical, $R_4$ represents a hydrogen atom or a $C_1$–$C_4$ alkyl radical.

In formula (I) above, and when $R_3$ is other than a hydrogen atom, then $R_1$ and $R_2$ preferably represent a hydrogen atom and $R_3$ is preferably identical to $R_4$, and when $R_3$ represents a halogen atom, then $R_1$, $R_2$ and $R_4$ preferably represent a hydrogen atom.

Among the para-phenylenediamines of formula (I) above, mention may be made more particularly of para-phenylenediamine, para-toluylenediamine, 2-isopropyl-para-phenylenediamine, 2-(β-hydroxyethyl)-para-phenylenediamine, 2-(ε-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(ε-hydroxy-ethyl)-para-phenylenediamine, 4-amino-1-(β-methoxyethyl) aminobenzene and 2-chloro-para-phenylenediamine, and the addition salts thereof with an acid.

Among the bis(phenyl)alkylenediamines which can be used as oxidation bases in the dyeing process according to the invention, mention may be made in particular of the compounds corresponding to the formula (II) below, and the addition salts thereof with an acid:

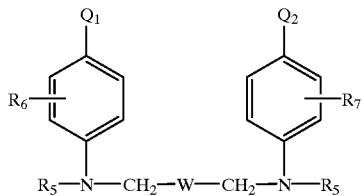

(II)

in which:

$Q_1$ and $Q_2$, which may be identical or different, represent a hydroxyl radical or a radical $NHR_8$ in which $R_8$ represents a hydrogen atom or a $C_1$–$C_4$ alkyl radical, $R_5$ represents a hydrogen atom, a $C_1$–$C_4$ alkyl, $C_1$–$C_4$ monohydroxyalkyl or $C_2$–$C_4$ polyhydroxyalkyl radical or a $C_1$–$C_4$ aminoalkyl radical in which the amino residue may be substituted, $R_6$ and $R_7$, which may be identical or different, represent a hydrogen or halogen atom or a $C_1$–$C_4$ alkyl radical, W represents a radical taken from the group consisting of the following radicals:

—$(CH_2)_n$; —$(CH_2)_m$—O—$(CH_2)_m$; —$(CH_2)_m$—CHOH—$(CH_2)_m$ and

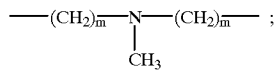

in which n is an integer between 0 and 8 inclusive and m is an integer between 0 and 4 inclusive.

Among the bis(phenyl)alkylenediamines of formula (II) above, mention may be made more particularly of N,N'-bis(β,-hydroxyethyl)-N,N'-bis(4'-aminophenyl)-1,3-diamino-2-propanol, N,N'-bis(β-hydroxyethyl) -N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine and N,N'-bis(ethyl)-N,N'-bis(4'-amino-3'-methyl-phenyl) ethylenediamine, and the addition salts thereof with an acid.

Among these bis(phenyl)alkylenediamines of formula (II), N,N'-bis(β-hydroxyethyl)-N,N'-bis(4'-aminophenyl)-1, 3-diamino-2-propanol, or one of its addition salts with an acid, is particularly preferred.

Among the para-aminophenols which can be used as oxidation bases in the dyeing process according to the invention, mention may be made in particular of the compounds corresponding to formula (III) below, and the addition salts thereof with an acid:

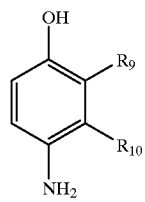

(III)

in which: $R_9$ represents a hydrogen atom or a $C_1$–$C_4$ alkyl, $C_1$–$C_4$ monohydroxyalkyl, $(C_1$–$C_4)$alkoxy$(C_1$–$C_4)$alkyl or $C_1$–$C_4$ aminoalkyl radical, $R_{10}$ represents a hydrogen or fluorine atom or a $C_1$–$C_4$ alkyl, $C_1$–$C_4$ monohydroxyalkyl, $C_2$–$C_4$ polyhydroxyalkyl, $C_1$–$C_4$ aminoalkyl, cyano$(C_1$–$C_4)$ alkyl or $(C_1$–$C_4)$alkoxy$(C_1$–$C_4)$alkyl radical, it being understood that at least one of the radicals $R_9$ and $R_{10}$ represents a hydrogen atom.

Among the para-aminophenols of formula (III) above, mention may be made more particularly of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the addition salts thereof with an acid.

Among the ortho-aminophenols which can be used as oxidation bases in the dyeing process according to the invention, mention may be made in particular of 2-aminophenol, 2-amino-1-hydroxy-5-methylbenzene, 2-amino-1-hydroxy-6-methylbenzene and 5-acetamido-2-aminophenol, and the addition salts thereof with an acid.

Among the heterocyclic bases which can be used as oxidation bases in the dyeing process according to the invention, mention may be made in particular of pyridine derivatives, pyrimidine derivatives and pyrazole derivatives, and the addition salts thereof with an acid.

Among the pyridine derivatives, mention may be made more particularly of the compounds described, for example, in patents GB-1,026,978 and GB-1,153,196, such as 2,5-diaminopyridine, and the addition salts thereof with an acid.

Among the pyrimidine derivatives, mention may be made more particularly of the compounds described, for example, in German patent DE-2,359,399 or Japanese patents JP-88-169,571 and JP-91-333,495, such as 2,4,5,6-tetraaminopyrimidine and 4-hydroxy-2,5,6-triaminopyrimidine, and the addition salts thereof with an acid.

Among the pyrazole derivatives, mention may be made more particularly of the compounds described in patents DE-3,843,892 and DE-4,133,957 and patent applications WO-94/08969 and WO-94/08970, such as 4,5-diamino-1-methylpyrazole and 3,4-diaminopyrazole, and the addition salts thereof with an acid.

According to the invention, the oxidation base(s) preferably represent(s) from 0.0005 to 12% by weight approximately relative to the total weight of the composition (A), and even more preferably from 0.005 to 6% by weight approximately.

The couplers which can be used in the dyeing process according to the invention are those used conventionally in oxidation dye compositions, i.e. meta-phenylenediamines, meta-aminophenols and meta-diphenols, and heterocyclic couplers such as, for example, indole derivatives and indoline derivatives, and the addition salts thereof with an acid.

These couplers can be chosen in particular from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 1,3-bis[(4-aminophenyl)(2-hydroxyethyl)amino]-2-propanol, sesamol, α-naphthol, 6-hydroxyindole, 4-hydroxyindole, 4-hydroxy-N-methylindole, 6-hydroxy-indoline, 2,6-dihydroxy-4-methylpyridine, 1H-3-methyl-5pyrazolone and 1-phenyl-3-methyl-5-pyrazolone, and the addition salts thereof with an acid.

When they are present, these couplers preferably represent from 0.0001 to 10% by weight approximately relative to the total weight of the composition (A) and even more preferably from 0.005 to 5% by weight approximately.

In general, the addition salts with an acid of the oxidation bases and couplers are chosen in particular from the hydrochlorides, hydrobromides, sulphates, tartrates, lactates and acetates.

The composition (A) also conventionally contains reducing agents in order to prevent the premature oxidation of the oxidation dye precursors; the said reducing agents are in particular, in a known manner, sodium bisulphite, thioglycolic acid and thiolactic acid, and the salts thereof. They are present in a proportion ranging from about 0.5 to 3% by weight, and preferably 0.1 to 1.5% by weight approximately, relative to the total weight of the composition (A).

The direct dyes which can be used in the dyeing process according to the invention are those used conventionally in direct dye compositions, and in particular nitrobenzene dyes, such as nitrophenylenediamines, nitrodiphenylamines, nitroanilines, nitrophenyl ethers, nitrophenols or nitropyridine dyes, anthraquinone dyes, monoazo or diazo dyes, azine dyes, acridine dyes and xanthene dyes, or metalliferous dyes.

However, according to the invention, it is more particularly preferred to use cationic direct dyes.

Among these, mention may be made advantageously of 3-[(4-amino-6-bromo-5,8-dihydro-1-hydroxy-8-imino-5-oxo-2-naphthalenyl)amino]-N,N,N-trimethylbenzenaminium chloride (referred to as Basic Blue 99 in the Color Index), as well as cationic direct dyes which contain a quaternized nitrogen atom which is possibly delocalizable and a bond —Z=N—, in which Z denotes a nitrogen atom or a —CH—radical, and in particular those corresponding to formula (IV) below:

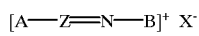

(IV)

in which Z denotes a nitrogen atom or a —CH—radical, A and B denote benzenic or heterocyclic aromatic groups which are optionally substituted, preferably with one or more halogen atoms or with one or more radicals such as $NR_{11}R_{12}$ or $OR_{11}$, in which $R_{11}$ and $R_{12}$, simultaneously or independently of each other, represent hydrogen, a $C_1$–$C_8$ alkyl radical, a $C_1$–$C_4$ hydroxyalkyl radical or a phenyl radical, X⁻denotes an anion, preferably chloride or methylsulphate, the cationic charge being borne by one of the substituents on the ring A and/or on the ring B.

These compounds of formula (IV) are described and prepared, for example, in the international patent applications WO-95/01772 and WO-95/15144 from the company Ciba-Geigy.

Among the compounds of formula (IV), mention may be made, for example, of the compounds of formulae (10) to (14) below:

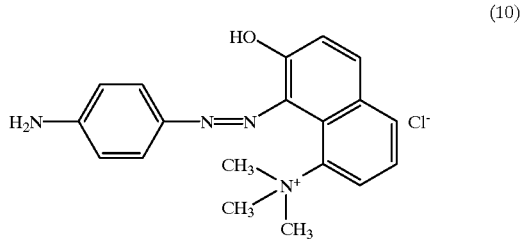

(10)

i.e. 4-aminophenylazo-2-hydroxy-8-trimethylammonionaphthalene chloride;

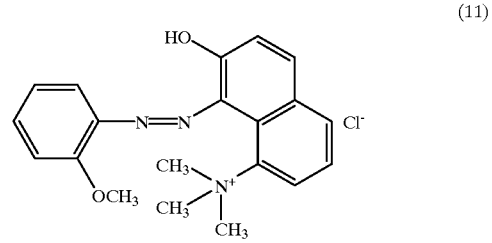

(11)

i.e. 2-methoxyphenylazo-2-hydroxy-8-trimethylammonionaphthalene chloride;

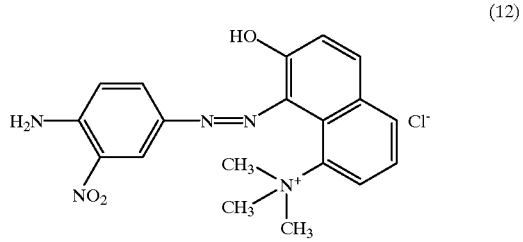

(12)

i.e. 4-amino-3-nitrophenylazo-2-hydroxy-8-trimethylammonionaphthalene chloride,

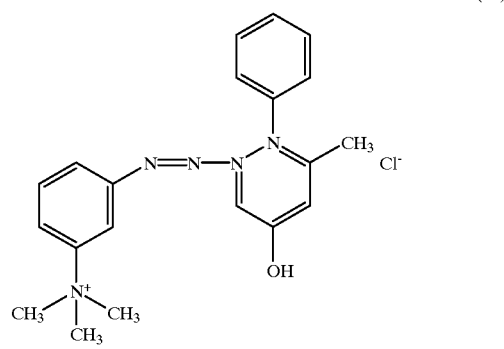

(13)

i.e. 3-trimethylammoniophenylazo-N-phenyl-3-methyl-5-hydroxypyridazine chloride;

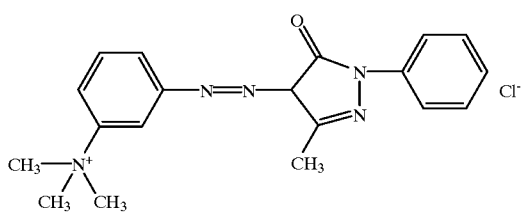

(14)

i.e. 3-[(4,5-dihydro-3-methyl-5-oxo-1-phenyl-1H-pyrazol-4-yl)azo]-N,N,N-trimethylbenzenaminium chloride.

The direct dyes preferably represent from 0.1 to 100% by weight approximately relative to the total weight of the composition (B), and even more advantageously 1 to 50% by weight approximately.

In the composition (C), the oxidizing agent is preferably chosen from hydrogen peroxide, urea peroxide, alkali metal bromates and persalts such as perborates and persulphates. It is particularly preferred to use hydrogen peroxide.

The oxidizing composition (C) advantageously consists of a hydrogen peroxide solution whose titre can range, more particularly, from 5 to 40 volumes approximately.

The medium for compositions (A) and optionally (C), which is suitable for dyeing, is preferably an aqueous medium consisting of water and/or cosmetically acceptable organic solvents, and more particularly alcohols such as ethanol, isopropanol, benzyl alcohol and phenylethyl alcohol, or glycols or glycol ethers such as, for example, ethylene glycol and its monomethyl, monoethyl and monobutyl ethers, propylene glycol or its ethers such as, for example, propylene glycol monomethyl ether, butylene glycol, dipropylene glycol and diethylene glycol alkyl ethers such as, for example, diethylene glycol monoethyl ether or monobutyl ether, in concentrations of between about 0.5 and 20%, and preferably between about 2 and 10%, by weight relative to the total weight of the composition.

The compositions (A) and (C) can also contain an effective amount of other agents, which are moreover previously known in oxidation dyeing, such as anionic, cationic, nonionic, amphoteric or zwitterionic surfactants or mixtures thereof, thickeners and various common adjuvants such as sequestering agents, hair conditioners, preserving agents, opacifiers, etc.

In the powdered composition (B), the direct dye can constitute the entire composition by itself, or can be dispersed in an excipient, in powder form, of organic nature and/or of inorganic nature. This powder preferably has a particle size of less than 350 μm.

The organic excipient can be of synthetic or plant origin and chosen in particular from crosslinked or non-crosslinked synthetic polymers, polysaccharides such as modified or unmodified celluloses and starches as well as natural products containing them such as sawdust, or plant gums (guar gum, carob gum, xanthan gum, etc.).

The inorganic excipient can consist of metal oxides such as titanium oxides, aluminium oxides, kaolin, talc, silicates, mica and silicas.

An advantageously preferred excipient consists of sawdust.

The powdered composition (B) can also contain binders or coating products in an amount preferably not exceeding 3% by weight approximately relative to the total weight of the said composition.

These binders are preferably oils or liquid fatty substances of inorganic, synthetic, animal or plant origin.

The powdered composition (B) can optionally also contain other adjuvants, in powder form, in particular surfactants of any nature, hair conditioners such as, for example, cationic polymers, etc.

Needless to say, a person skilled in the art will take care to select the optional complementary compound(s) mentioned above such that the advantageous properties intrinsically associated with the dye composition according to the invention are not, or are not substantially, adversely affected by the addition(s) envisaged.

The relative amounts of the compositions (A), (B) and (C) in the dyeing process according to the present invention preferably range, expressed in parts by weight, from about 1/0.010/0.5 to 1/1/4 and even more preferably from 1/0.05/0.5 to 1/0.5/2.

The pH of the ready-to-use dye composition containing three components (A), (B) and (C), in accordance with the invention, which is applied to the fibres is generally between 3 and 12. It is preferably between the values 8.5 and 11 and can be adjusted to the desired value using acidifying or basifying agents that are well known in the state of the art in the dyeing of keratin fibres.

Among the basifying agents, mention may be made, for example, of aqueous ammonia, alkaline carbonates, alkanolamines such as mono-, di- and triethanolamines and derivatives thereof, sodium hydroxide, potassium hydroxide and the compounds of formula (V) below:

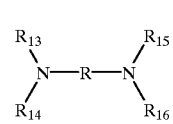

(V)

in which R is a propylene residue optionally substituted with a hydroxyl group or a $C_1$–$C_4$ alkyl radical; $R_{13}$, $R_{14}$, $R_{15}$ and $R_{16}$ which may be identical or different, represent a hydrogen atom or a $C_1$–$C_4$ alkyl or $C_1$–$C_4$ hydroxyalkyl radical.

The acidifying agents are conventionally, for example, inorganic or organic acids such as hydrochloric acid, orthophosphoric acid, carboxylic acids such as tartaric acid, citric acid or lactic acid, or sulphonic acids.

The dyeing process according to the invention preferably consists in applying a mixture, prepared extemporaneously at the time of use from the three components (A), (B) and (C) described above, to the dry or wet keratin fibres, and in leaving this mixture to act for an exposure time preferably ranging from 1 to 60 minutes approximately, and more preferably from 10 to 45 minutes approximately, rinsing the fibres, then optionally washing them with shampoo and then rinsing them again and drying them.

Concrete examples illustrating the invention will now be given without, however, being limiting in nature.

EXAMPLES

Example 1

| Composition (A): | |
|---|---|
| oleyl alcohol polyglycerolated with 2 mol of glycerol | 4.0 g |
| oleyl alcohol polyglycerolated with 4 mol of glycerol, containing 78% active material (A.M.) | 5.69 g A.M. |

| Composition (A): | |
| --- | --- |
| oleic acid | 3.0 g |
| oleylamine containing 2 mol of ethylene oxide, sold under the trade name Ethorneen 012 by the company Akzo | 7.0 g |
| dimethylaminopropyl laurylamino succinamate, sodium salt, containing 55% A.M. | 3.0 g A.M. |
| oleyl alcohol | 5.0 g |
| oleic acid diethanolamide | 12.0 g |
| propylene glycol | 3.5 g |
| ethanol | 7.0 g |
| diethylene glycol monobutyl ether | 0.5 g |
| propylene glycol monomethyl ether | 9.0 g |
| sodium metabisulphite as an aqueous solution containing 35% A.M. | 0.455 g A.M. |
| ammonium acetate | 0.8 g |
| para-phenylene diamine | 0.35 g |
| 1,3 dihydroxybenzene | 0.4 g |
| 3-aminophenol | 0.03 g |
| 2,4-diamino-1-(β-hydroxyethyloxy)benzene dihydrochloride | 0.012 g |
| 1,3-bis[(4-aminophenyl) (2-hydroxyethyl) amino]-2-propanol tetrahydrochloride | 0.037 g |
| 1,3-dihydroxy-2-methylbenzene | 0.2 g |
| antioxidant, sequestering agent | q.s. |
| fragrance, preserving agent | q.s. |
| aqueous ammonia containing 20% NH$_3$ | 10.0 g |
| demineralized water q.s. | 100 g |

| Composition (B) | |
| --- | --- |
| powdered cationic direct dye of formula (II) | 20 g |
| liquid paraffin | 3 g |
| powdered cationic polymer (Merquat 280 Dry from Calgon) | 10 g |
| sawdust q.s. | 100 g |

| Composition (C) | |
| --- | --- |
| 20-volume hydrogen peroxide | 100 g |

1 part by weight of composition (A) was mixed, at the time of use, with 0.1 part by weight of composition (B) and 1 part by weight of composition (C).

The pH of the resultant composition was 9.8.

This composition was then applied to locks of natural or permanent-waved grey hair containing 90% white hairs. After an exposure time of 30 minutes, rinsing with running water, washing with a standard shampoo and drying, the locks were dyed in a red-dark blonde shade, this dyeing showing satisfactory resistance towards atmospheric agents, perspiration and the various treatments to which the hair may be subjected.

What is claimed is:

1. A process for dyeing keratin fibers comprising applying an extemporaneous mixture to said keratin fibers, wherein said extemporaneous mixture comprises:
   (a) composition (a) containing at least one oxidation dye precursor and optionally at least one coupler, in a medium suitable for dyeing;
   (b) composition (b) in powder form containing at least one cationic direct dye, optionally dispersed in an excipient chosen from organic excipients and inorganic excipients; and
   (c) composition (c) containing at least one oxidizing agent in a medium suitable for dyeing,
   wherein composition (a), composition (b) and composition (c) are mixed extemporaneously at the time of application to said keratin fibers in a weight ratio of 1/0.01/0.5 to 1/1/4 respectively, and
   wherein the organic excipients and inorganic excipients are in either pulverulent or powder form.

2. A process according to claim 1, wherein said keratin fibers are human keratin fibers.

3. A process according to claim 2, wherein said human keratin fibers are hair.

4. A process according to claim 1, wherein said at least one direct dye is 3-[(4-amino-6-bromo-5,8-dihydro-1-hydroxy-8-imino-5-oxo-2-naphthalenyl)amino]-N,N,N-trimethylbenzenaminium chloride.

5. A process according to claim 1, wherein said at least one direct dye contains a possibly delocalizable quaternized nitrogen atom and a bond —Z=N=, wherein Z denotes a nitrogen atom or a —CH—radical.

6. A process according to claim 1, wherein said at least one direct dye is a compound of formula (IV):

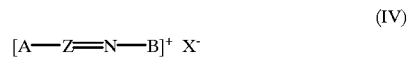

in which:

Z denotes a nitrogen atom or a -CH- radical,

A and B independently denote benzenic or heterocyclic aromatic groups which are optionally substituted, and X$^-$ denotes an anion,
   wherein one of A or B is substituted with a substituent which bears the cationic charge.

7. A process according to claim 6, wherein A and/or B are optionally substituted with at least one halogen atom or with at least one radical NR$_{11}$,R$_{12}$ or with at least one radical OR$_{11}$, wherein R$_{11}$ and R$_{12}$ independently represent hydrogen, a C$_1$–C$_8$ alkyl radical, a C$_1$–C$_4$ hydroxyalkyl radical or a phenyl radical.

8. A process according to claim 6, wherein X$^-$ denotes chloride or methylsulphate.

9. A process according to claim 6, wherein said at least one direct dye is chosen from formulae 10 to 14:

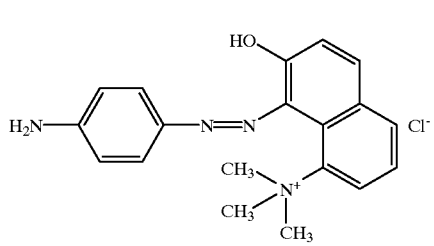

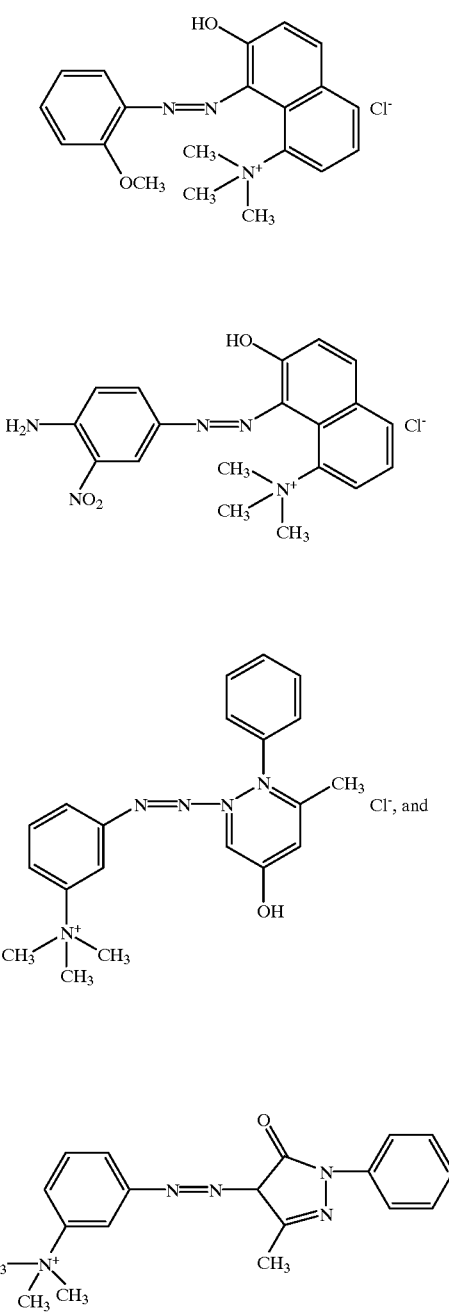

10. A process according to claim 1, wherein said at least one direct dye is present in an amount ranging from 0.1 to 100% by weight relative to the total weight of said composition (b).

11. A process according to claim 10, wherein said at least one direct dye is present in an amount ranging from 1 to 50% by weight relative to the total weight of said composition (b).

12. A process according to claim 1, wherein in said composition (a), said at least one oxidation dye precursor is selected from ortho-phenylenediamines, para-phenylenediamines, bis(phenyl)alkylenediamines, ortho-aminophenols, para-aminiphenols, heterocyclic bases, and acid addition salts thereof.

13. A process according to claim 1, wherein said at least one oxidation dye precursor is present in an amount ranging from 0.0005 to 12% by weight relative to the total weight of said composition (a).

14. A process according to claim 13, wherein said at least one oxidation dye precursor is present in an amount ranging from 0.005 to 6% by weight relative to the total weight of said composition (a).

15. A process according to claim 1, wherein in said composition (a), said at least one coupler is selected from meta-phenylenediamines, meta-aminophenols, meta-diiphenols, heterocyclic couplers, and acid addition salts thereof.

16. A process according to claim 1, wherein said at least one coupler is present in an amount ranging from 0.0001 to 10% by weight relative to the total weight of said composition (a).

17. A process according to claim 16, wherein said at least one coupler is present in an amount ranging from 0.005 to 5% by weight relative to the total weight of said composition (a).

18. A process according to claim 15, wherein said acid addition salts are selected from hydrochlorides, hydrobromides, sulphates, tartrates, lactates and acetates.

19. A process according to claim 12, wherein said acid addition salts are selected from hydrochlorides, hydrobromides, sulphates, tartrates, lactates and acetates.

20. A process according to claim 1, wherein said composition (a) further comprises at least one reducing agent.

21. A process according to claim 20, wherein said at least one reducing agent is selected from sodium bisulphite, thioglycolic acid, thiolactic acid, and salts thereof.

22. A process according to claim 20, wherein said at least one reducing agent is present in an amount ranging from 0.05 to 3% by weight relative to the total weight of said composition (a).

23. A process according to claim 22, wherein said at least one reducing agent is present in an amount ranging from 0.1 to 1.5% by weight relative to the total weight of said composition (a).

24. A process according to claim 1, wherein in said composition (c), said at least one oxidizing agent is selected from hydrogen peroxide, urea peroxide, alkali metal bromates, and persalts.

25. A process according to claim 24, wherein in said composition (c), said at least one oxidizing agent is hydrogen peroxide.

26. A process according to claim 1, wherein said composition (c) is a hydrogen peroxide solution with a titre ranging from 5 to 40 volumes.

27. A process according to claim 1, wherein in said composition (b), said at least one direct dye is dispersed in said excipient.

28. A process according to claim 27, wherein said at least one direct dye is dispersed in sawdust.

29. A process according to claim 1, wherein said compositions (a), (b) and (c) are present in parts by weight ranging from 1:0.05:0.5 to 1:0.5:2.

30. A process according to claim 1, wherein said medium suitable for dyeing is an aqueous medium.

31. A process according to claim 30, wherein said aqueous medium comprises water or water and at least one cosmetically acceptable organic solvent.

32. A process according to claim 31, wherein said at least one cosmetically acceptable organic solvent is selected from alcohols, glycols, and glycol ethers.

33. A process according to claim 1, wherein said at least one direct dye of composition (b) is a powder having a particle size of less than 350 μm.

34. A process according to claim 1, wherein said composition (b) further comprises at least one binder or at least one coating product.

35. A process according to claim 34, wherein said at least one binder or at least one coating product is present in an amount no greater than 3% by weight relative to the total weight of said composition (b).

36. A process according to claim 17, wherein said composition (b) further comprises at least one cosmetically acceptable adjuvant, in a powder form.

37. A process according to claim 1, wherein said keratin fibers are wet or dry and after said applying, leaving said extemporaneous mixture on said keratin fibers for an exposure time ranging from 1 to 60 minutes, rinsing said keratin fibers, optionally washing said keratin fibers with shampoo and rinsing again, and drying said keratin fibers.

38. A process according to claim 37, wherein said exposure time ranges from 10 to 45 minutes.

39. A multi-compartment device for dyeing keratin fibers, comprising at least three compartments, wherein a first compartment contains composition (a) comprising at least one oxidation dye precursor and optionally at least one coupler, in a medium suitable for dyeing, a second compartment contains composition (b) in polyerulent or powder form comprising at least one cationic direct dye in powder form optionally dispersed in an excipient chosen from organic and inorganic excipients, and a third compartment contains composition (c) comprising at least one oxidizing agent in a medium suitable for dyeing, wherein said compositions (a), (b) and (c) are present in said device in parts by weight ranging for 1/0.01/0.5 to 1/1/4 respectively.

40. A multi-compartment device of claim 39 wherein said device is a kit.

* * * * *

UNITED STATES PATENT AND TRADEMARK OFFICE
CERTIFICATE OF CORRECTION

PATENT NO. : 6,190,421 B1
DATED : February 20, 2001
INVENTOR(S) : Rondeau et al.

It is certified that error appears in the above-identified patent and that said Letters Patent is hereby corrected as shown below:

<u>Claim 7, column 10,</u>
line 46, change "$NR_{11,}R_{12}$" to -- $NR_{11}R_{12}$ --.

Signed and Sealed this

Fourth Day of September, 2001

Attest:

*Nicholas P. Godici*

NICHOLAS P. GODICI
*Attesting Officer*  *Acting Director of the United States Patent and Trademark Office*